United States Patent [19]

Paragamian et al.

[11] 3,985,880

[45] Oct. 12, 1976

[54] 2-(R'-OXYMETHYL)-PERIMIDINES

[75] Inventors: Vasken Paragamian, Dresher, Pa.; Russell J. Taylor, Jr., Palmyra, N.J.

[73] Assignee: McNeil Laboratories, Incorporated, Fort Washington, Pa.

[22] Filed: Feb. 7, 1975

[21] Appl. No.: 548,063

Related U.S. Application Data

[63] Continuation-in-part of Ser. No. 380,983, July 19, 1973, abandoned.

[52] U.S. Cl.............................. 424/251; 260/251 Q
[51] Int. Cl.²................ A61K 27/00; C07D 239/00
[58] Field of Search................. 260/251 Q; 424/251

[56] References Cited

UNITED STATES PATENTS 3,502,647   3/1970   Paragamian .................... 260/251 Q

*Primary Examiner*—Frederick E. Waddell

[57] ABSTRACT

Certain perimidines are observed to be useful antiulcer agents in view of their activity as inhibitors of gastric acid secretion and ulcer formation. Among such antiulcer agents are novel 2-(R'-oxymethyl)-perimidine derivatives, wherein R¹ is a member selected from the group consisting of benzoyl, carbamyl, N-loweralkylcarbamyl, and N,N-diloweralkylcarbamyl.

14 Claims, No Drawings

2-(R'-OXYMETHYL)-PERIMIDINES

REFERENCE TO PRIOR ART

This application is a continuation-in-part of our co-pending application Ser. No. 380,983, filed July 19, 1973, now abandoned.

DESCRIPTION OF THE INVENTION:

This invention relates to the antiulcer activity of perimidine derivatives having the formula:

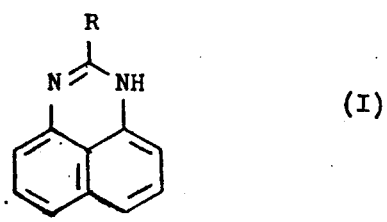

wherein R is a member selected from the group consisting of hydrogen, loweralkyl, cyanoloweralkyl, mercaptoloweralkyl, hydroxyloweralkyl, carbamyl, loweralkanoyloxymethyl, benzoyloxymethyl, carbamyloxymethyl, N-loweralkyl-carbamyloxymethyl, N,N-diloweralkyl-carbamyloxymethyl, loweralkoxyloweralkyl, amino-loweralkyl, N-loweralkylamino-loweralkyl, and N,N-diloweralkylamino-loweralkyl; and the therapeutically active, non-toxic acid addition salts thereof.

As used herein, loweralkyl and loweralkoxy may be straight or branch chained and have from 1 to 5 carbon atoms, such as, for example, methyl, ethyl, propyl, isopropyl, butyl, tert-butyl, pentyl and the like alkyls, and, respectively, the corresponding alkoxys, e.g., methoxy, ethoxy, etc.

The compounds of formula (I) have been, for the most part, previously described, for example, see U.S. Pat. No. 3,502,647 and F. Sachs, Ann. 365, 53 (1909), and are prepared according to general procedures described in the literature and available to one skilled in the art. Certain compounds of formula (I), however, are deemed to be novel, namely; those wherein R is a member selected from the group consisting of benzoyloxymethyl, carbamyloxymethyl N-loweralkyl-carbamyloxymethyl and N,N-diloweralkylcarbamyloxymethyl, as further illustrated by the following formula:

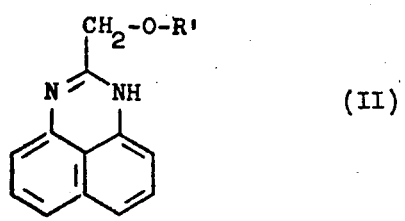

in which R' is a member selected from the group consisting of benzoyl, carbamyl, N-loweralkylcarbamyl and N,N-diloweralkyl-carbamyl; and the therapeutically active acid addition salts thereof.

The perimidines of formula (I) are useful antiulcer agents as shown, for example, by their ability to inhibit gastric acid secretion and inhibit ulcer formation in standard laboratory animal tests. For example, antisecretory activity is observed in the 3-hour pyloric-ligated rat test at an intraperitoneal (i.p.) or oral dose of about 10–100 mg/kg body weight.

The test procedure is a modification of the Shay et al. technique reported in Gastroenterology, 26, 906 (1954). Male Sprague-Dawley rats (CFE, 180–220 g), in individual cages, are allowed access solely to a solution of 8% sucrose and 0.2% sodium chloride ad libitum for 48 hours prior to administration of the compound to be tested. One hour after administration of the compound, the rat is anesthetized with ether, the pylorus is exposed by a mid-line laparotomy and tied off with surgical thread, and the incision is closed with autoclips. Three hours later the rat is sacrificed by cervical dislocation. The incision is reopened, the esophagus is clamped at the cardiac sphincter, and the entire stomach is excised. The stomach is cut open and the contents are allowed to drain into a centrifuge tube. The mucosa is washed with 2 ml of saline and the wash is added to the contents. The stomach contents are centrifuged at 600 × gravity for 30 minutes, after which the supernatant is decanted, mixed with 10 ml of saline and titrated to pH 7 using 0.02N sodium hydroxide. The number of equivalents of sodium hydroxide used is a measure of the amount of acid produced. The less sodium hydroxide required, the less gastric acid produced, and the more effective the inhibition.

The compound to be tested is dissolved or suspended in an aqueous solution (containing 0.05% Tween 80) at appropriate concentrations so that oral or i.p. administration of 1 ml per 100 g of rat weight gives the proper dosage. Since most of the compounds are insoluble in water, they may be tested by dissolving in either 0.01N hydrochloric acid (for i.p. dosing) or 3% lactic acid (for oral dosing). In all studies, five animals are used per group, and the results compared to those obtained from experimental controls. According to this test, it has been found that at least 25% inhibition of gastric acid secretion, as compared with controls, are obtained at i.p. or oral doses of about 10–100 mg/kg of the subject compounds (I) in base or acid addition salt form.

Typical examples of compounds included within the scope of formula (I) and their antisecretory activity are shown hereinafter in Table 1. It is understood that such examples are not listed therein for purposes of limiting the invention thereto, but only to exemplify the useful properties of all the compounds within the scope of formula (I), including the therapeutically active acid addition salts thereof.

TABLE 1.

Effect on Gastric Acid Secretion in Rats at Intraperitoneal Doses of 50 mg/kg.

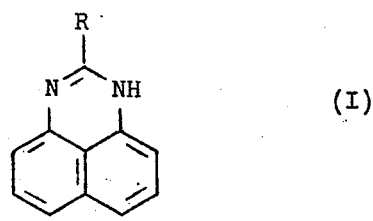

Table 1—Continued

| R | Gastric Acid Secreted (-equiv. H$^+$/3 hrs.) Control | Treated | % Inhibition |
|---|---|---|---|
| —H | 535 ± 55 | 150 ± 122 | 72 |
| —CH$_3$ | 395 ± 60 | 57 ± 11 | 86 |
| —CH$_2$CN* | 670 ± 51 | 89 ± 36 | 87 |
| —CH$_2$SH* | 670 ± 51 | 195 ± 120 | 71 |
| —CH$_2$OH | 670 ± 51 | 192 ± 33 | 71 |
| —CH(CH$_3$)OH | 566 ± 112 | 192 ± 23 | 66 |
| —C(CH$_3$)$_2$OH* | 496 ± 126 | 134 ± 45 | 73 |
| —C(CH$_3$)(C$_2$H$_5$)OH* | 427 ± 126 | 150 ± 22 | 65 |
| —CONH$_2$ | 670 ± 51 | 117 ± 50 | 83 |
| —CH$_2$OCOCH$_3$ | 496 ± 126 | 79 ± 13 | 84 |
| —CH$_2$OCOC$_2$H$_5$* | 427 ± 107 | 222 ± 48 | 48 |
| —CH$_2$OCO~Ph | 472 ± 55 | 244 ± 74 | 48 |
| —CH$_2$OCONH$_2$* | 422 ± 83 | 73 ± 16 | 83 |
| —CH$_2$OCH$_3$ | 727 ± 73 | 118 ± 21 | 84 |
| —C(CH$_3$)$_2$CH$_2$N(CH$_3$)$_2$ | 496 ± 126 | 131 ± 29 | 74 |
| —CH$_2$OCONHCH$_3$ | 727 ± 73 | 171 ± 36 | 76 |

*HCl salt

In addition to their antisecretory action, the compounds of formula (I) are active inhibitors of ulcer formation, as demonstrated in acid-induced or stress-induced ulcer tests on laboratory animals. For example, the subject compounds (I) in base or acid addition salt form, are observed to inhibit the formation of acid-induced ulcers in the pyloric-ligated rat at an oral dose of about 10–100 mg/kg body weight by the technique of H. Shay, et al. Gastoenterology, 5, 43 (1945), and I. L. Bonta, Arch. Int. Pharmacodyn., 132, 147 (1961).

According to this procedure, male Sprague-Dawley rats (CFE, 160–180g) are allowed only water ad libitum for 48 hours prior to use and are housed in individual cages. The compound to be tested is administered orally one hour prior to surgical ligation of the pylorus (as described heretofore). After 18 hours, the rats are sacrificed by cervical dislocation; and the stomachs are removed and placed in 10% buffered formalin for 1 minute. The stomachs are then rinsed with water, blotted and examined for ulcers, which are generally found in the nonglandular, upper half of the stomach. The number of ulcers and the severity thereof are determined. The severity is rated on the basis of the approximate diameter of the ulcer according to the following scale:

| Approximate Diameter (mm) | Score |
|---|---|
| <0.9 | 0.5 |
| 1.0-1.9 | 1 |
| 2.0-2.9 | 2 |
| 3.0-3.9 | 4 |
| >4.0 | 8 |
| Perforation | 16 |

Stomachs found to be free of ulcers, but demonstrating a moderate hyperemia, are scored 0.5 for each area. Perforated ulcers are scored 16. The data is represented as the "ulcer-score," which is the sum of the number of ulcers per stomach plus the severity rating for each ulcer. The average ulcer score for each group of 5 rats is compared to the experimental control value and to the cumulative control value for the percent inhibition at a given dose. A statistical evaluation is made of both sets of data using the Student-t test; the inhibition is considered significant if $p < .05$ or not significant if $p > .05$.

The compounds of formula (I) are also active in inhibiting the formation of stress-induced stomach ulcers in the cold, restrained rat at oral doses of about 10–100 mg/kg body weight. In this model there is a development of ulcers in the glandular mucosal region of the rat's stomach. The rat has been shown to be a useful model for the study of stress-induced ulcers in humans, which is an important cause of morbidity in a variety of clinical situations [see R. Lambert, Prog. Gastroenteral, 1, 40 (1968); E. Eisman and R. L. Hegman, N. Engl. J. Med., 282, 372 (1920)].

In this procedure, male Wistar rats (140–180 g, Carsworth Farms, CFN) are allowed only water ad libitum for 24 hours prior to testing. One hour after oral administration of test compounds (or vehicle), the rats are immobilized by placing each of them in a tight-fitting wire mesh cylinder (7 inches × 2 inches in diameter) closed at one end. A piston-like wooden plug is inserted into the open end and is adjusted to the rat size. The plug is held in place with U-shaped pin, and the tail of the rat (which exits through a hole in the cylinder) is taped to the outside of the cylinder. Immediately upon being restrained, the rats are placed in a room at 4° C for 2 hours, after which time they are removed from the cylinders and are sacrificed by cervical dislocation. The stomachs are removed, inflated with 5 ml of water and placed in a buffered solution of 10% formalin for 1 minute, and then rinsed with water. The stomachs are then cut open along the greater curvature, the insides rinsed with water, and pinned open on a cork-board for counting of ulcers.

In view of the antiulcer activity of the subject compounds, there is provided herein a method of aiding the prevention and amelioration of ulcers which comprises internally administering to an ulcer-prone subject a pharmaceutical composition comprising an effective antiulcer amount of a member selected from the group consisting of a perimidine of formula (I) and a therapeutically active non-toxic, acid addition salt thereof in admixture with a pharmaceutical carrier.

To prepare the pharmaceutical compositions of this invention, a perimidine derivative of formula (I) or salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharamceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the care of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, particularly with the water-soluble salts of formula (I), though other ingredients, for example, to aid solubility or for preservative purposes, may be included. Injectable suspensions may also be prepared, particularly with the bases of formula (I), in which case appropriate liquid carriers, suspending agents and the like may be employed. The pharmaceutical compositions herein will contain, per dosage unit, e.g., tablet, capsule, powder, injection, teaspoonful and the like, from about 5 to about 500 mg of the active ingredient, and, preferably, from about 10 to about 250 mg.

The compounds of formula (I) may be converted to the corresponding therapeutically active non-toxic acid addition salt form by reaction with an appropriate inorganic acid, such as, for example, hydrochloric, hydrobromic, hydriodic, sulfuric, phosphoric, nitric and the like acids, or with an appropriate organic acid, such as, for example, acetic, propionic, glycolic, lactic, oxalic, malonic, sulfamic, p-toluenesulfonic and the like acids. In turn, the acid addition salts may be converted to the corresponding free base form by conventional treatment with suitable alkali.

The novel compounds of formula (II) may be prepared from 2-perimidinemethanol (III). For example, by reacting this precursor with an appropriate acid anhydride (IV) of the formula, $(R_1CO)_2O$, or with an appropriate acid chloride (V) of the formula, $R_1COCl$, wherein $R_1$ is phenyl, there are obtained those com- To prepare the novel carbamate derivatives of formula (II), 2-perimidinemethanol (III) is reacted with a loweralkyl chloroformate (VI) in a suitable organic solvent, such as, for example, dimethoxyethane, diglyme, tetrahydrofuran, dimethylformamide or an aromatic hydrocarbon such as benzene, toluene, xylene and the like. The reaction is conducted in the presence of a strongly basic catalyst, such as, for example, an alkali metal hydride or amide, e.g., sodium hydride and sodium amide, respectively, and is generally allowed to proceed for about 4 to 8 hours at temperatures between 20° to 80° C. The thus-obtained oxazolidinone intermediate (VII) is then treated with a primary, secondary or tertiary amine (VIII) of the formula, $HNR_2R_3$, wherein each of $R_2$ and $R_3$ are members selected from the group consisting of hydrogen and loweralkyl, in a suitable organic solvent as mentioned previously for about 4–10 hours at temperatures of about 20°–50° C. According to the reaction conditions employed, the desired carbamates (IX) may be isolated as free bases or in the form of acid addition salts.

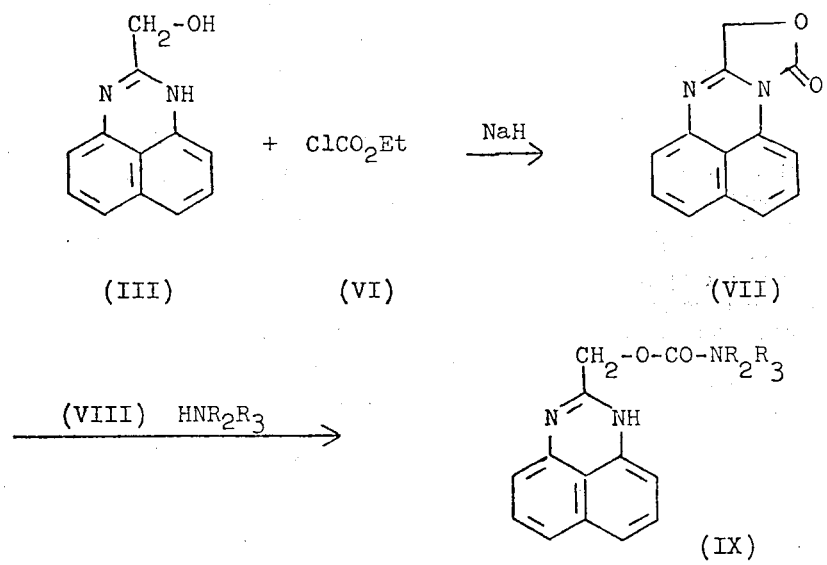

pounds of formula (II) where $R^1$ is benzoyl. Reaction conditions generally employed for reacting an alcohol with an acid anhydride or chloride are applicable. For example, the reaction may be conducted in the absence of solvent at elevated temperatures e.g., 80°–100° C, for about 3–6 hours in the case of the anhydride, or in a suitable inert solvent, e.g., an aromatic hydrocarbon such as benzene, toluene, xylene and the like, under reflux for about 6–10 hours in the case of the acid chloride. The products (VI) in base form may be transformed to therapeutically active acid addition salts by conventional treatment with suitable acids.

The following examples are intended to illustrate, but not to limit, the scope of the present invention.

EXAMPLE I

α-Methyl-2-perimidinemethanol

A mixture of 32 g (0.2 mole) of 1,8-diaminonaphthalene and 32 g (0.3 mole) of 85% lactic acid in 400 ml of 4N hydrochloric acid is refluxed for 18 hr. The separated solid is filtered and converted to the free base by treatment with dilute ammonia for 2 hr. The new solid is filtered and recrystallized twice from 95% ethanol to

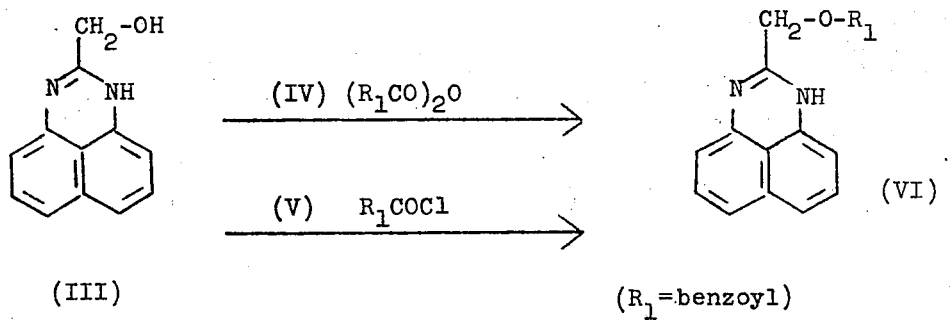

give the product, α-methyl-2-perimidinemethanol, as yellow crystals, m.p. 205°–206° dec.

Anal. Calcd. for $C_{13}H_{12}N_2O$:N, 13.20. Found: N(D), 13.09.

EXAMPLE II

α,α-Dimethyl-2-perimidinemethanol hydrochloride 1,8-Diaminonaphthalene (24 g 0.15 mole) and 23 g (0.22 mole) a α-methyllactic acid are refluxed in 350 ml of 4N hydrodiloric acid for 3 days. After cooling, the separated solids are filtered and washed repeatedly with water, then recrystallized (charcoal) from water to give the desired product, α,α-dimethyl-2-perimidinemethanol hydrochloride, as yellow crystals, m.p. 266°–267° C.

Anal. Calcd. for $C_{14}H_{14}N_2O$ HCl: C, 64.00; H, 5.76; N, 10.66. Found: C, 64.17; H, 5.67; N(K), 10.96.

EXAMPLE III

α-Ethyl-α-methyl-2-perimidinemethanol hydrochloride 1,8-Diaminonaphthalene (44.5 g, 0.282 mole) is suspended in 400 ml of 4N hydrochloric acid. To this suspension is added 2-hydroxy-2-methyl butyric acid (50 g, 0.423 mole) and the whole is stirred and heated under reflux for 96 hours. Then the reaction mixture is allowed to cool and is filtered, yielding a gray-green solid. The solid is heated and stirred with 1 liter of refluxing ethanol, and is filtered while hot to remove unreacted starting materials. The filtrate is concentrated to dryness and the resulting solid is treated with 500 ml of boiling ethanol. After the insoluble material is removed by filtration, the filtrate was treated with charcoal, yielding a yellow solution. Addition of ether, plus cooling, yields a yellow-brown solid. Recrystallization from ethanol (charcoal) yields the desired product, α-ethyl-α-methyl-2-perimidinemethanol, hydrochloride, m.p. 266°–268° dec.).

Anal. Calcd. for $C_{15}H_{16}N_2O$ HCl: C, 65.10; H, 5.83; N, 10.12. Found: C, 65.27; H, 5.71; N, 10.31, 10.36. N,

EXAMPLE IV

1H, 3H-Oxazolo[3,4-a]perimidine-3-one

Equivalent quantities of 2-perimidinemethanol and sodium hydride are heated for ½ hour in dimethoxyethane. After the evolution of hydrogen has stopped, ethyl chloroformate is added to the solution, and the resulting mixture is stirred for 3 hours, poured into water and the separated solid collected and recrystallized twice from dimethoxyethane to give the desired product, 1H, 3H-oxazolo[3,4-a]perimidine-3-one, m.p. 194°–195°.

EXAMPLE V

(2-Perimidyl)methylcarbamate hydrochloride

A sample of 1H, 3H-oxazolo[3,4-a]perimidine-3-one is dissolved in dimethoxyethane and is treated with excess conc. ammonia. The separated solid, (2-perimidyl)methyl carbamate, is filtered, dissolved in ethanol and treated with hydrochloric acid to give the acid addition salt, (2-perimidyl)methyl carbamate hydrochloride, m.p. 240° (dec.).

EXAMPLE VI

(2-Perimidyl)methyl N,N-dimethylcarbamate

A 10 g (0.44 mole) sample of 1H, 3H-oxazolo[3,4-a]perimidine, 3-one is dissolved in glyme at 30°, and the resulting solution is treated with excess 40% aqueous dimethylamine for 10 min. The mixture is then concentrated, dissolved in $CHCl_3$, washed with water and dried. Further concentration gives an oil which is crystallized from ethyl acetate-cylcohexane and is then recrystallized from the same solvents twice to give the desired product, (2-perimidyl)methyl N,N-dimethylcarbamate, as yellow crystals, m.p. 161°–162° C.

Anal. Calcd. for $C_{15}H_{15}N_3O_2$: C, 66.90; H, 5.61; N, 15.61. Found: C, 66.61; H, 5.55; H, 15.53.

EXAMPLE VII

(2-Perimidyl)methyl benzoate

2-Perimidinemethanol (10 g, .05 mole) and benzoic anhydride (12 g, 0.053 mole) are mixed, then melted and heated on a steam bath for 5 min. A yellow solid results which is taken up in chloroform-water and is treated with ammonia. The separated solid is filtered off and the chloroform layer is dried and concentrated to give a yellow solid. These solids are combined and are recrystallized from ethyl acetate to give the desired product, (2-perimidyl)methyl benzoate, as yellow crystals, m.p. 164°–165°.

Anal. Calcd. for $C_{19}H_{14}N_2O_2$: C, 75.48; H, 4.67; N, 9.27. Found: C, 75.01; H, 5.14; N, 9.40.

EXAMPLE VIII

The procedure of Example VI is repeated except that an equivalent quantity each of methylamine, n-butylamine and diethylamine is used in place of the dimethylamine used therein to yield, as respective products:

(2-perimidyl)methyl N-methylcarbamate;
(2-perimidyl)methyl N-(n-butyl)carbamate; and
(2-perimidyl)methyl N,N-diethylcarbamate.

EXAMPLE IX-CAPSULES 10,000 Hard gelatin capsules, each containing as the active ingredient (A.I.) 50 mg of (2-perimidyl)methyl N-methylcarbamate, are prepared from the following formulation:

|  | Grams |
|---|---|
| A.I. | 500 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

EXAMPLE X - TABLETS 5,000 Compressed tablets, each containing as the active ingredient (A.I.) 10 mg of (2-perimidyl)methyl carbamate hydrochloride, are prepared from the following formulation:

| | Grams |
|---|---|
| A.I. | 50 |
| Starch | 75 |
| Dibasic Calcium phosphate, hydrous | 500 |
| Calcium Stearate | 2.5 |

The finely powdered ingredients are mixed well and are granulated with 10% starch paste. The granulation is dried and compressed into tablets using starch as the disintegrant and calcium stearate as the lubricant.

EXAMPLE XI - INJECTABLE

The following formulation provides 1 liter of a parenteral suspension comprising 15 mg of 2-methoxymethyl perimidine as the active ingredient per milliliter:

| | Grams |
|---|---|
| A.I. | 15.0 |
| Polysorbate 80 | 2.0 |
| Sodium chloride | 9.0 |
| Sodium Carboxymethyl cellulose | 10.0 |
| Methyl paraben | 1.8 |
| Propyl paraben | 0.2 |
| Water for Injection, U.S.P., q.s. ad | 1 liter |

Dissolve the parabens, sodium chloride, and carboxymethyl cellulose in ½ the total volume of water by heating to 95° C to obtain a clear solution. Filter and autoclave. Dissolve the polysorbate in ⅓ the total volume of water. Filter and autoclave this second solution. Add sterile A.I. to the second solution and pass it through a sterile colloid mill. To the resulting suspension add the first solution with uniform stirring. Q.s. with sterilized water and stir while filling into sterile vials.

EXAMPLE XII - INJECTABLE

The following formulation provides 1 liter of a parenteral solution comprising 25 mg of (2-perimidyl)methyl carbamate hydrochloride as the active ingredient per milliliter:

| | Grams |
|---|---|
| A.I. | 25.0 |
| Water for Injection, U.S.P., q.s. ad 1 liter | |

The solution is autoclaved to insure sterility and placed into sterile vials. Bacteriostatic agents commonly employed as adjuvants in parenteral solutions may be added to the above formulation.

EXAMPLE XIII - ORAL SUSPENSION

The following formulation provides 5 liters of an oral suspension comprising 100 mg of (2-perimidyl)methyl N,N-dimethylcarbamate as the active ingredient per teaspoonful (5 mls):

| | Grams |
|---|---|
| A.I. | 100.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow No. 5 | 0.1 |
| Sodium cyclamate | 50.0 |
| Sodium saccharin | 5.0 |
| Orange flavor | 7.5 |
| Filtered purified water, q.s. ad 5 liters | |

Dissolve the parabens in the propylene glycol and add this solution to a solution of the sodium cyclamate, sodium saccharin and sucrose in half the water. Suspend the bentonite in hot (about 85° C) water and stir for 60 minutes. Add the bentonite solution to the former solution. Dissolve the sulfosuccinate in some water and suspend the A.I. in the resulting solution. Add the Antifoam A.F. Emulsion which has been diluted to a lotion consistency with a minimum amount of water and mix well. Add the latter suspension of A.I. to the former mixture and mix well. Add the FD&C Yellow No. 5 dissolved in a small amount of water. Add the orange flavor, q.s. to volume with water, and stir to a homogeneous mixture. Pass the mixture through a colloid mill and fill into suitable containers.

The foregoing pharmaceutical compositions are examples of unit dosages suitable for internal administration to man or other warm blooded animals for anti-ulcer purposes.

We claim:
1. The method of aiding the prevention and amelioration of stomach ulcers which comprises internally administering to a subject having stomach ulcers a pharmaceutical composition useful for treatment of said stomach ulcers in dosage unit form comprising per dosage unit from about 5 to about 500 mg of a member selected from the group consisting of a perimidine compound having the formula:

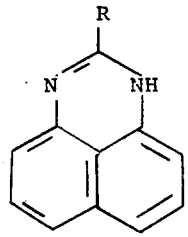

wherein R is a member selected from the group consisting of hydrogen, loweralkyl, cyanoloweralkyl, mercaptoloweralkyl, hydroxyloweralkyl, carbamyl, loweralkanoyloxymethyl, benzoyloxymethyl, carbamyloxymethyl, N-loweralkyl-carbamyloxymethyl, N,N-diloweralkyl-carbamyloxymethyl, loweralkoxy-loweralkyl, amino-loweralkyl, N-loweralkyl amino-loweralkyl and N, N-diloweralkylamino-loweralkyl, said loweralkyl and said loweralkoxy being straight or branch chained and having from 1 to 5 carbon atoms, and a therapeutically active acid addition salt thereof, as an active ingredient in admixture with a pharmaceutically acceptable carrier.

2. The method of aiding the prevention and amelioration of stomach ulcers which comprises internally administering to a subject having stomach ulcers a pharmaceutical composition useful for treatment of said stomach ulcers in dosage unit form comprising per dosage unit from about 5 to about 500 mg of a member selected from the group consisting of a permidine compound having the formula:

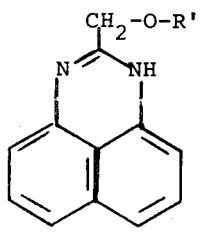

wherein R' is a member selected from the group consisting of benzoyl, carbamyl, N-loweralkyl-carbamyl and N,N-diloweralkylcarbamyl, said loweralkyl being straight or branch chained and having from 1 to 5 carbon atoms, and a therapeutically active acid addition salt thereof, as an active ingredient in admixture with a pharmaceutically acceptable carrier.

3. The method of claim 1 wherein R is hydrogen.
4. The method of claim 1 wherein R is methyl.
5. The method of claim 1 wherein R is carbamyl.
6. The method of claim 1 wherein R is carbamyloxymethyl.
7. The method of claim 1 wherein R is methoxymethyl.
8. The method of claim 1 wherein the dosage unit form is a tablet.
9. The method of claim 1 wherein the dosage unit form is a capsule.
10. A pharmaceutical composition useful for treatment of stomach ulcers in dosage unit form comprising from about 5 to about 500 mg of a member selected from the group consisting of a perimidine compound having the formula:

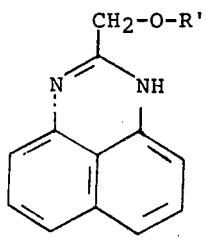

wherein R' is a member selected from the group consisting of benzoyl, carbamyl, N-loweralkyl-carbamyl and N,N-diloweralkylcarbamyl, said loweralkyl being straight or branch chained and having from 1 to 5 carbon atoms, and a therapeutically active acid addition salt thereof, as an active ingredient in admixture with a pharmaceutically acceptable carrier.

11. A compound selected from the group consisting of a perimidine having the formula:

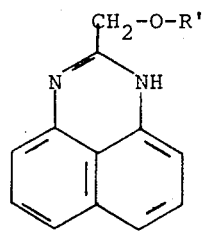

wherein R' is a member selected from the group consisting of benzoyl, carbamyl, N-loweralkyl-carbamyl and N,N-diloweralkylcarbamyl, said loweralkyl being straight or branch chained and having from 1 to 5 carbon atoms, and a therapeutically active acid addition salt thereof.

12. A compound selected from the group consisting of (2-perimidyl)methyl carbamate and a therapeutically active acid addition salt thereof.

13. (2-Perimidyl)methyl N,N-dimethylcarbamate.

14. (2-Perimidyl)methyl benzoate.

* * * * *